United States Patent [19]

Lisnyansky

[11] 4,350,889

[45] Sep. 21, 1982

[54] X-RAY FLUORESCENT ANALYSIS WITH MATRIX COMPENSATION

[75] Inventor: Khaim Lisnyansky, Central Valley, N.Y.

[73] Assignee: International Paper Company, New York, N.Y.

[21] Appl. No.: 188,046

[22] Filed: Sep. 17, 1980

[51] Int. Cl.³ .......................................... G01M 23/22
[52] U.S. Cl. ..................................... 378/46; 378/53
[58] Field of Search ........... 250/272, 273, 274, 277 R, 250/278, 279

[56] References Cited

U.S. PATENT DOCUMENTS

| | | | |
|---|---|---|---|
| 3,114,832 | 12/1963 | Alvarez | 250/51.5 |
| 3,375,369 | 3/1968 | Goldman | 250/273 |
| 3,660,662 | 5/1972 | Puolakka | 250/83.3 D |
| 3,861,199 | 1/1975 | Barkhoudarian | 73/67.5 R |
| 4,047,029 | 9/1977 | Allport | 250/273 |
| 4,081,676 | 3/1978 | Buchnea | 250/272 |
| 4,169,228 | 9/1979 | Briska et al. | 250/272 |

FOREIGN PATENT DOCUMENTS 171482 4/1971 U.S.S.R. .
491883 4/1976 U.S.S.R. .

OTHER PUBLICATIONS

Buchnea et al., "On-Line Nondestructive Paper Chemistry Analysis by X-Ray Fluorescence," *Amer. Nucl. Soc. Trans.*, vol. 22, pp. 146-148 (1975).
Considine (editor), *Van Nostrand's Scientific Encyclopedia*, pp. 2353-2356 (5th ed. 1976).
Considine (editor), *Process Instruments and Controls Handbook*, pp. 6-41 to 6-42, (2nd ed. 1974); three pages on "X-Ray Fluorescence Analytical Methods", (1st ed. 1957).
Frevert et al., "On-line Non-Contacting Determination of Ash Content in Fast-Moving Paper Webs," *Industrial Measurement and Control by Radiation Techniques*, pp. 208-214 (1972).
Lucas-Tooth et al., "The Accurate Determination of Major Constituents by X-Ray Fluorescent Analysis in the Presence of Large Interelement Effects," *Advances in X-Ray Analysis*, vol. 7, pp. 523-541, (1964).
Lucas-Tooth et al., "A Mathematical Method for the Investigation of Inter-Element Effects in X-Ray Fluorescent Analysis," *Metallurgia*, vol. 64, pp. 149-152 (1961).
McNelles et al., "An On-line Ash Constituent Determination Using X-Ray Fluorescence", (date and place of publication uncertain).
Stern et al., *X-rays*, pp. 31-35, 202-211, (1970).
Vander, "Method of Measurement of Mean Concentration for an Element Segregated in Layers by X-Ray Analysis," Barrett (editor), *Advances In X-Ray Analysis*, vol. 21, pp. 143-147, (1978).
"A New Moisture Insensitive Method for Measurement of Paper and Board Coating Weights", Puumalainen *Tappi*, vol. 63, No. 7, Jul. 1980, pp. 55-57.

Primary Examiner—Craig E. Church
Attorney, Agent, or Firm—Stephen P. Gilbert

[57] ABSTRACT

A new X-ray fluorescence method for testing a sample having two essentially parallel planar faces that provides full matrix effect compensation is disclosed. The intensities of the transmitted and fluorescent beams of photons are measured by X-ray detectors, and the X-ray source and the two detectors are operated so that $$\frac{\sin \phi}{\sin \psi} \cong \frac{(E_2)^3}{(E_1)^3}$$

where $\Phi$ is the angle of the primary beam to one face of the sample, $\Psi$ is the angle of the fluorescent beam to either face of the sample, $E_1$ is the energy of the photons of the primary beam, and $E_2$ is the characteristic electron orbital transition energy for the element of interest. From the ratio of the two intensities the mean average concentration of the element is calculated directly without iterative or other complex procedures.

8 Claims, 3 Drawing Figures

Fig. 1.

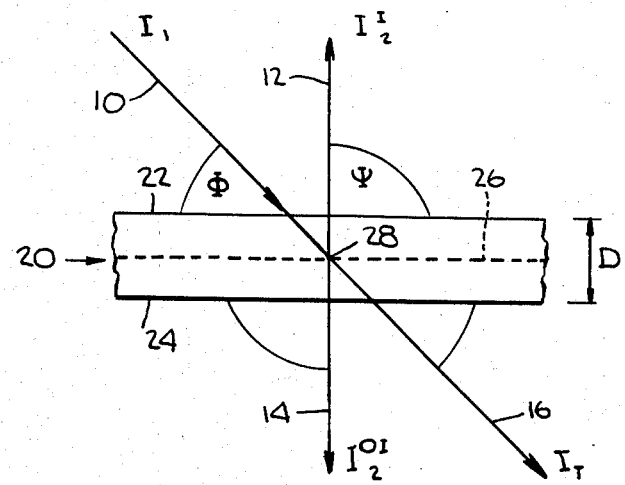

Fig. 2A.

(1) $\quad I_2^I = K \dfrac{C_A}{\frac{\mu m_1}{\sin\Phi} + \frac{\mu m_2}{\sin\Psi}} \left[ 1 - e^{-\left(\frac{\mu m_1}{\sin\Phi} + \frac{\mu m_2}{\sin\Psi}\right)d} \right]$ (2) $\quad \mu m_1 = \mu m_{A,1} C_A + \mu m_{M,1}(1 - C_A)$ (3) $\quad \mu m_2 = \mu m_{A,2} C_A + \mu m_{M,2}(1 - C_A)$ (4) $\quad I_T = I_1\, e^{-\dfrac{[\mu m_{A,1} C_A + \mu m_{M,1}(1-C_A)]d}{\sin\Phi}}$ (5) $\quad \dfrac{I_2^I}{I_T} = \dfrac{K}{I_1} \dfrac{C_A}{\frac{\mu m_1}{\sin\Phi} + \frac{\mu m_2}{\sin\Psi}} \left[ e^{\frac{\mu m_1}{\sin\Phi} d} - e^{-\frac{\mu m_2}{\sin\Psi} d} \right]$ (6) $\quad e^{\frac{\mu m_1}{\sin\Phi} d} = 1 + \dfrac{\mu m_1}{\sin\Phi} d + \dfrac{1}{2} \dfrac{\mu^2 m_1}{\sin^2\Phi} d^2 + \dfrac{1}{6} \dfrac{\mu^3 m_1}{\sin^3\Phi} d^3 + \ldots$ (7) $\quad e^{-\frac{\mu m_2}{\sin\Psi} d} = 1 - \dfrac{\mu m_2}{\sin\Psi} d + \dfrac{1}{2} \dfrac{\mu^2 m_2}{\sin^2\Psi} d^2 - \dfrac{1}{6} \dfrac{\mu^3 m_2}{\sin^3\Psi} d^3 + \ldots$

Fig. 2B.

(8) $\quad \dfrac{I_2^I}{I_T} = \dfrac{K}{I_1} C_{Ad}$ (9) $\quad e^{\frac{\mu m_1}{\sin \Phi} d} \cong 1 + \dfrac{\mu m_1}{\sin \Phi} d \quad \text{AND} \quad e^{-\frac{\mu m_2 d}{\sin \Psi}} \cong 1 - \dfrac{\mu m_2}{\sin \Psi} d$

(10) $\quad \dfrac{\mu m_1}{\sin \Phi} d \ll 1 \quad \text{AND} \quad \dfrac{\mu m_2}{\sin \Psi} d \ll 1$

(11) $\quad \dfrac{I_2^I}{I_T} = \dfrac{K}{I_1} C_A d \left[ 1 + \dfrac{1}{2}\left(\dfrac{\mu m_1}{\sin \Phi} - \dfrac{\mu m_2}{\sin \Psi}\right) d \right]$

(12) $\quad \dfrac{\sin \Phi}{\sin \Psi} \cong \left(\dfrac{E_2}{E_1}\right)^3$

(13) $\quad \dfrac{\sin \Phi}{\sin \Psi} = \dfrac{\mu m_{M,1}}{\mu m_{M,2}}$

(14) $\quad \dfrac{I_2^I}{I_T} = \dfrac{K}{I_1} C_A d \left[ 1 + \dfrac{1}{2}\left(\dfrac{\mu m_{A,1}}{\sin \Phi} - \dfrac{\mu m_{A,2}}{\sin \Psi}\right) C_A d \right]$

(15) $\quad \dfrac{I_2^I}{I_T} = \dfrac{K}{I_1} C_A d \left[ 1 + \dfrac{1}{2}\left(\dfrac{\mu m_{A,1}}{\sin \Phi} - \dfrac{\mu m_{A,2}}{\sin \Psi}\right) C_A d + \dfrac{1}{6}\left(\dfrac{\mu m_1^2}{\sin^2 \Phi} d^2 + \dfrac{\mu m_2^2}{\sin^2 \Psi} d^2 - \dfrac{\mu m_1 \cdot \mu m_2}{\sin \Phi \cdot \sin \Psi} d^2\right) \right]$

(16) $\quad I_2^{OI} = K_1 \dfrac{C_A}{\dfrac{\mu m_1}{\sin \Phi} - \dfrac{\mu m_2}{\sin \Psi}} \left( e^{-\frac{\mu m_2}{\sin \Psi} d} - e^{-\frac{\mu m_1}{\sin \Phi} d} \right)$

(17) $\quad \dfrac{I_2^{OI}}{I_T} = \dfrac{K_1}{I_1} \dfrac{C_A}{\dfrac{\mu m_1}{\sin \Phi} - \dfrac{\mu m_2}{\sin \Psi}} \left[ e^{\left(\frac{\mu m_1}{\sin \Phi} - \frac{\mu m_2}{\sin \Psi}\right) d} - 1 \right]$

(18) $\quad \dfrac{I_2^{OI}}{I_T} = \dfrac{K_1}{I_1} \dfrac{1}{\dfrac{\mu m_{A,1}}{\sin \Phi} - \dfrac{\mu m_{A,2}}{\sin \Psi}} \left[ e^{\left(\frac{\mu m_{A,1}}{\sin \Phi} - \frac{\mu m_{A,2}}{\sin \Psi}\right) C_A d} - 1 \right]$

(19) $\quad \dfrac{I_2^{OI}}{I_T} = K_2 \left[ e^{\left(\frac{\mu m_{A,1}}{\sin \Phi} - \frac{\mu m_{A,2}}{\sin \Psi}\right) C_A d} - 1 \right]$

(20) $\quad K_2 = \dfrac{K_1}{I_1 \left(\dfrac{\mu m_{A,1}}{\sin \Phi} - \dfrac{\mu m_{A,2}}{\sin \Psi}\right)}$

X-RAY FLUORESCENT ANALYSIS WITH MATRIX COMPENSATION

BACKGROUND OF THE INVENTION

Various analytical methods employing X-rays are well-known. See, e.g., *Van Nostrand's Scientific Encyclopedia*, "X-ray Analysis," pp 2353–2356 (5th ed. 1976); Stern et al., *X-rays*, pp. 31–35 and 202–211 (1970); Frevert et al., "On-line Non-contacting Determination of Ash Content in Fast-moving Paper Webs," *Industrial Measurement and Control by Radiation Techniques*, pp. 208–214 (1972); and U.S. Pat. Nos. 4,047,029, 3,861,199, and 3,114,832.

In particular, X-ray fluorescence is well-known (see, e.g. Considine (editor), *Process Instruments and Controls Handbook*, "X-ray Fluorescence Analytical Methods," (1st ed. 1957) and "X-ray Fluorescence Analysis,"(2nd ed. 1974), and U.S. Pat. No. 4,169,228) and has been used in the paper industry. See, e.g., Puumalalnen et al., "A new moisture-insensitive method for measurement of paper and board coating weights," *TAPPI*, vol. 63, no. 7, pp. 55–57 (1980); Buchnea et al., "On-line Nondestructive Paper Chemistry Analysis by X-ray Fluorescence," *Am. Nucl. Soc. Trans.*, vol. 22, pp. 146–148 (1975); McNelles et al., "An On-line Ash Constituent Determination Using X-ray Fluorescence"; and U.S. Pat. Nos. 4,081,676 and 3,660,662.

This technique is based on the discovery years ago that if atoms of an element are excited by photons of sufficient energy (primary beam), those atoms will give off photons having energy characteristic of that element (fluorescent or secondary radiation). In practice, however, analyzing the fluorescent radiation data to determine how much of a particular element is present in a sample is made complex by what may be called the "position effect" and by the so-called "matrix effect," which significantly influence the data.

The position effect arises when the element of interest is not uniformly distributed throughout the sample, that is, when there is a concentration gradient. Various techniques have been suggested for eliminating the position effect. See, e.g., U.S.S.R. Pat. No. 491,883 and Vander, "Method of Measurement of Mean Concentration for an Element Segregated in Layers by X-ray Analysis," *Advances in X-ray Analysis*, vol. 21, pp. 143–147 (1978). They suggest that the fluorescence be measured from the non-irradiated side of the sample and that the apparatus be arranged to satisfy the equation $$\frac{\mu_{M,1}}{\mu_{M,2}} = \frac{\csc \Psi}{\csc \Phi}$$

where $\mu_{M,1}$ and $\mu_{M,2}$ are the mass absorption coefficients of the matrix for the incident (or primary) beam and for the fluorescent beam, respectively, and $\Psi$ and $\Phi$ are the angles of the fluorescent and incident beams, respectively, to the sample.

Of greater significance, however, is the matrix effect, which occurs because of the presence of elements in the sample in addition to the element of interest. The other elements may cause the concentration of the element of interest calculated from the test data to be significantly higher or lower than the actual concentration.

Numerous techniques have been suggested to compensate for the matrix effect. Some involve iterative solution of simultaneous equations in which the concentration of each element is an unknown. This, in turn, requires the use of a computer. (Even then, the solution may not be mathematically stable.) See, e.g., Lucas-Tooth et al., "The Accurate Determination of Major Constituents by X-ray Fluorescent Analysis in the Presence of Large Interelement Effects," *Advances in X-ray Analysis*, vol. 7, pp. 523–541 (1964); and Lucas-Tooth et al., "A Mathematical Method for the Investigation of Inter-Element Effects in X-ray Fluorescent Analysis," *Metallurgia*, vol. 64, pp. 149–152 (1961).

Another technique for compensating for the matrix effect is disclosed in U.S.S.R. Pat. No. 171,482. This method utilizes the ratio between fluorescent and scattering radiation; however, accurate discrimination between fluorescent photons and scattered photons having energies close to the fluorescent photons is difficult.

Another technique that involves matrix compensation when assaying for three specific components in a web such as paper is disclosed in U.S. Pat. No. 4,081,676. Various assumptions are made initially and expected absorption is compared to actual absorption.

Yet another method involving matrix compensation when assaying for four specific components in paper is disclosed in Puumalalnen et al., above. Absorption data and fluorescence data from both sides of the sample are utilized in an iterative procedure.

Each of these matrix compensation techniques has drawbacks.

SUMMARY OF THE INVENTION

A new X-ray fluorescence method that offers full matrix compensation has now been discovered. The method involves aiming a beam of primary photons at the sample so that the beam hits a first surface of the sample at angle $\Phi$ and aiming a first detector at the second surface of the sample to detect the unabsorbed primary photons. A second detector to detect fluorescent X-rays is then aimed at either the first or second surface at angle $\Psi$ wherein the following equation is satisfied for the element of interest:

$$\frac{\sin \phi}{\sin \psi} \cong \frac{(E_2)^3}{(E_1)^3}$$

$E_1$ and $E_2$ are, respectively, the energies of the photons of the primary and fluorescent radiation. Obviously, for a given orbital transition for a given element, $E_2$ is fixed; however, $E_1$ and the two angles are variable. The ratio of fluorescence intensity to transmission intensity is then used to calculate the concentration of the element of interest. In preferred embodiments, $\Psi$ is 90 degrees and the secondary beam being detected intersects the line of the primary beam at an imaginary plane parallel to and half-way between the two faces of the sample.

This method offers numerous advantages compared to previously known methods. Data on the presence of elements not being assayed for are not needed, thus saving time and money. Iterative calculation methods are not needed, thus complex computers and computer programs are not needed. The accuracy of the method seems to be significantly higher, particularly when testing layered samples or samples where the fluorescence is measured from the surface opposite that being irradiated by the primary beam. The sensitivities $(\Delta I/I)/(\Delta C_A/C_A)$ [I is the intensity or ratio of intensities and $C_A$ is the concentration of element A] of the new and old methods are equal at low concentrations, but as the concentration increases, the sensitivity of the new method also increases while that of the old decreases, and the same is true for changes in surface density. There is full compensation for the position effect.

DESCRIPTION OF THE DRAWINGS

In order to more fully describe the invention, the following drawings are provided in which FIG. 1 shows the primary and secondary X-rays to and from a sample tested in accordance with the present invention;

FIG. 2 shows equations relating to the present invention; and

DETAILED DESCRIPTION OF THE INVENTION

Figure 3:
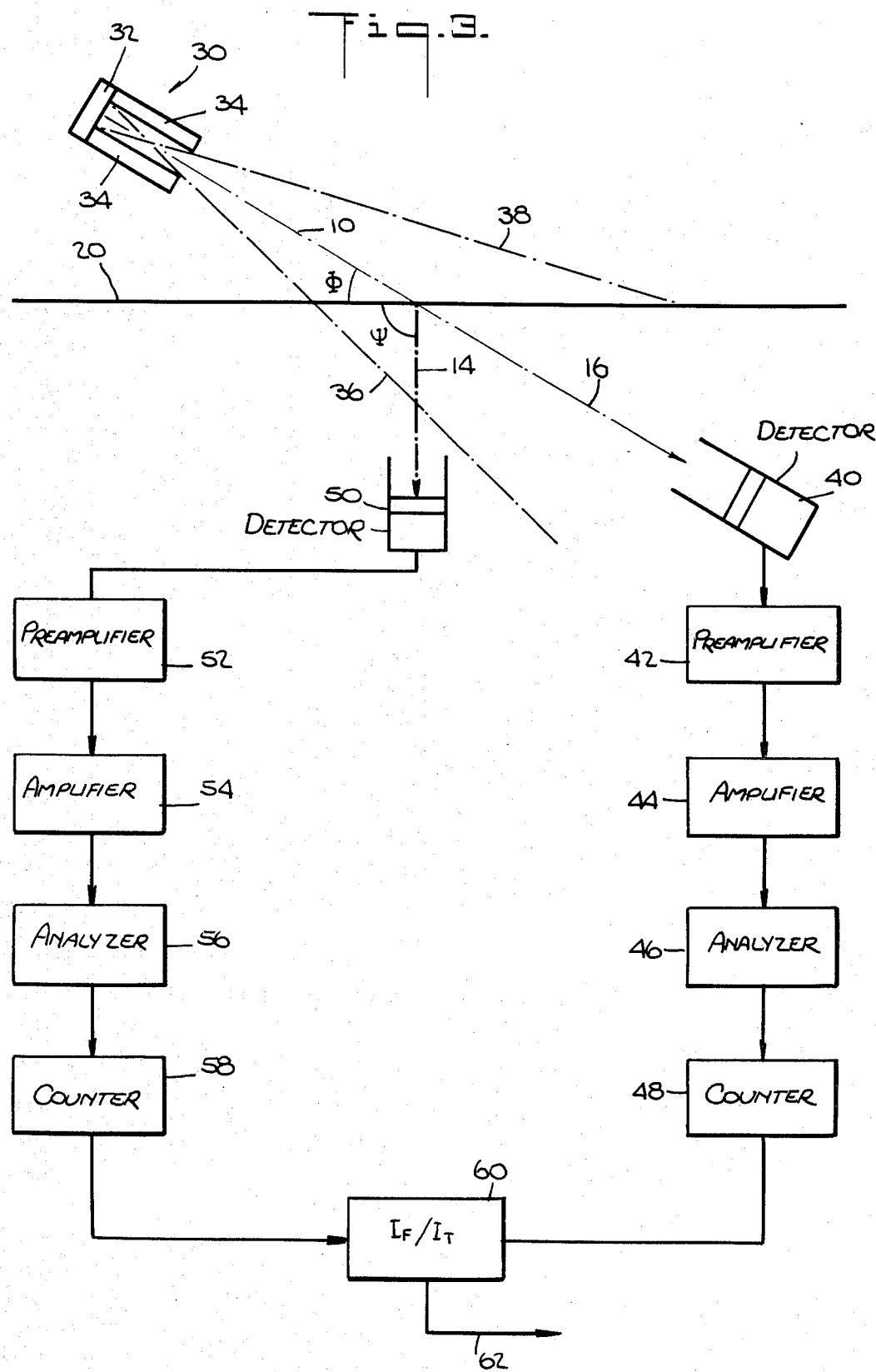
FIG. 3 is a schematic diagram of a system embodying the present invention.

Radiation is a probabilistic phenomenon and the amount of radiation at a given energy level is determined as the number of counts per unit time (intensity I) recorded by a radiation detector for a range of energy levels bracketing to given degree the given energy level.

Referring to FIG. 1, $I_1$ is the intensity of beam 10 of primary photons of energy $E_1$ aimed at sample 20 of thickness D. Sample 20 has essentially parallel first and second faces 22 and 24, respectively. Plane 26 is parallel to and half-way between the faces of the sample. $I_T$ is the intensity of beam 16 of transmitted primary photons, which pass through sample 20 without being absorbed. Line 10–16 intersects plane 26 at point 28 and is at angle $\Phi$ to faces 22 and 24.

Beams 12 and 14 are beams of intensities $I_2^I$ and $I_2^{OI}$, respectively, of secondary (or fluorescent) photons having an energy level $E_2$ characteristic of the element of interest (the one being assayed for). Line 12–14 forms angle $\Psi$ with faces 22 and 24.

Sample thickness D (units of length) is related to the surface density (units of mass per surface area) by the density (units of mass per volume). Surface density (d) is also known as grammage or basic weight.

The energy level of the photons of primary beam 10 must be great enough to cause the atoms of interest to become excited so that they will emit their characteristic secondary radiation. For example, when testing paper to determine the amount of $TiO_2$ present, the titanium may be assayed for using a primary beam of photons having an energy higher than 5.0 kev (i.e., above the K absorption edge of the element). That is sufficient energy since the L to K electron orbital transition emits a photon of 4.5 kev.

The present method requires measuring the intensity of transmitted beam 16 and of either fluorescent beam 12 or 14. For beam 12, equation (eqn.) 1 (FIG. 2) may be written. In that equation, K is a complicated constant that takes into account various factors, including $I_1$, the geometry of the test site, and the atomic constant. K is independent of the sample composition. $C_A$ is the concentration of the element of interest, element A, in the matrix M, d is the surface density, and $\mu_{m1}$ and $\mu_{m2}$ are the mass absorption coefficients of the sample for the primary and secondary beams 10 and 12, respectively. "Sin" is the standard abbreviation for the triginometric function sine, and "e" is the base for natural logarithms.

The two overall mass absorption coefficients [units of (length)$^2$/mass] are weighted average factors defined by eqns. 2 and 3. $\mu_{mA,1}$ and $\mu_{mM,1}$ are, respectively, the mass absorption coefficients of element A and matrix M (everything in the sample other than element A) for the primary X-ray. $\mu_{mA,2}$ and $\mu_{mM,2}$ are, respectively, the mass absorption coefficients of A and M for the secondary (or fluorescent) X-rays.

For the intensity $I_T$ of beam 16, eqn. 4 is valid. Eqn. 5 results from dividing eqn. 1 by eqn. 4 and from the definition of $\mu_{m1}$ in eqn. 2.

The exponential expressions in eqn. 5 may be written as the infinite series given in eqns. 6 and 7. Substituting the first two terms of eqns. 6 and 7 for the exponentials in eqn. 5, eqn. 8 may be obtained.

In eqn. 8, the ratio $I_2^I/I_T$ is independent of the mass absorption coefficients and is insensitive to the presence of elements other than A in the sample (matrix effect). However, substituting the first two terms of the series of eqns. 6 and 7 into eqn. 5 is valid if the conditions of eqns. 10 are met, that is, only if the sample is very thin. (As will be understood by one skilled in the art, the maximum thickness for which eqns. 9 are correct depends on various factors, including the atomic number of the element A.)

If those equations are not valid, the first three terms of the series of eqns. 6 and 7 may be substituted for the exponentials of eqn. 5. After simplifying, eqn. 11 is obtained, which is sensitive to the matrix composition because of the definitions of $\mu_{m1}$ and $\mu_{m2}$ (eqns. 2 and 3).

If, however, angles $\Phi$ and $\Psi$ and energy $E_1$ are chosen so that equation 12 is fulfilled for element A ($E_2$ is obviously invariable for an element depending on which orbital transition is used—usually L to K or M to L), eqn. 11 can be reduced to a form free from matrix effects.

It is known that the mass absorption coefficients for X-ray energies up to approximately 120 kev are proportional to $E^{-3}$ ($\mu$ is a function of energy and atomic number). Substituting for $E_1$ and $E_2$, eqn. 13 is obtained. For all practical cases, primary energies of much less than 120 kev are needed. For example, energies as low as 5 kev are sufficient when assaying for titanium.

Using eqns. 2, 3, and 13, eqn. 14 can be derived from eqn. 11. In eqn. 14, the ratio $I_2^I/I_T$ is independent of the matrix effect ($\mu_{mA,1}$ and $\mu_{mA,2}$ are constant for fixed energy levels $E_1$ and $E_2$).

However, eqn. 14 was calculated using the first three terms of eqns. 6 and 7. If the first four terms are needed because of the thickness of the sample, eqn. 15 may be obtained from eqn. 5. Substitution as was done to obtain eqn. 14 from eqn. 11 cannot completely eliminate $\mu_{m1}$ and $\mu_{m2}$, and the interelement effect remains. The thicker the sample, the greater this effect.

Accordingly, when using the new method and measuring the fluorescent beam of photons from the same side of the sample as the primary beam is incident, full matrix compensation is achievable only when the sample is thin enough so that eqn. 8 or 14 is valid.

If, however, fluorescence is measured from the face of the sample opposite that being irradiated, full matrix compensation can be achieved with the present invention regardless of sample thickness.

For the intensity of the fluorescent beam 14 (FIG. 1), eqn. 16 may be written (see, e.g., Pivovarov et al., *Apparatus and Methods of X-ray Analysis* 11, p. 115 (1972)). All variables are as defined before except for $K_1$, which is a constant analogous to K in eqn. 1 and is independent of concentration $C_A$.

Dividing eqn. 16 by eqn. 4, eqn. 17 is obtained. Using eqns. 12 and 13 and the definitions in eqns. 2 and 3, eqn.

18 can be obtained, which can be further simplified to eqn. 19, where $K_2$ is defined in eqn. 20. Eqn. 19 is independent of both matrix and position effects.

FIG. 3 is a schematic showing use of the new invention. X-ray source 30 contains radioactive material 32 or X-ray tube 32 producing primary beams of photons aimed at one face of sample 20. Collimator 34 focuses the beams within the cone delimited by lines 36 and 38, and primary beam 10 forms angle $\Phi$ with sample 20 (see FIG. 1). Detector 40 is aimed at the second face of sample 20 to detect beam 16, the unabsorbed (or transmitted) portion of beam 10 exiting the sample.

Detector 50 is aimed at the second face of sample 20 to detect fluorescent radiation emanating therefrom. Detector 50 should be positioned so that it is outside the cone of primary radiation delimited by lines 36 and 38. (It will be understood that fluorescence detector 50 could instead be positioned above sample 20, corresponding to eqns. 1 through 15.) Whether above or below the sample, detector 50 will preferably be aimed at the point of intersection of the line of primary beam 10 and imaginery plane 26 (FIG. 1), which plane is parallel to and half-way between the two faces of the sample. In FIG. 1, the intersection of line 10–16 and plane 26 is at point 28. Accordingly, detection of fluorescent beam 14 (or 12) by detector 50, which beam intersects the line of primary beam 10 and plane 26 at point 28, is preferred. The angle between fluorescent beam 14 and face 24 (or between fluorescent beam 12 and face 22) is angle $\Psi$. Preferably, angle $\Psi$ is essentially 90 degrees, that is, beam 14 (or 12) being detected by fluorescence detector 50 is essentially perpendicular to the faces and mid-plane of sample 20 in the localized region being tested.

Returning to FIG. 3, the signals from detectors 40 and 50 pass, respectively, to preamplifiers 42 and 52, amplifiers 44 and 54, analyzers 46 and 56, counters 48 and 58, and divider 60, which calculates the ratio of the intensities of the fluorescent and transmitted radiation. Signal 62, containing the ratio information, may be fed to a digital display device, from which a human operator can utilize the ratio information to calculate $C_A$, or the signal may be fed to a control calculator to determine $C_A$ and adjust processing conditions, if necessary, to bring $C_A$ to the desired level.

$C_A$ may be determined in the following way. If fluorescence from the face opposite the primary beam is being detected, eqn. 19 is used. In eqns. 19 and 20, for a sample of known composition and thickness and a given apparatus, $\Psi$, $\Phi$, $C_A$, d, $I_1$, $I_T$, and $I_2^{OI}$ are chosen or are known from measurement and $\mu_{mA,1}$ and $\mu_{mA,2}$ are known from standard tables. (For example when using $Fe^{55}$ as the source, emitting photons of 5.9 kev, $\mu_{mA,1}$ for titanium is 435 cm$^2$/g and $\mu_{mA,2}$ for titanium for the L to K transition, 4.5 kev, is 83.5 cm$^2$/g.) The only unknown in equation 19 is $K_2$, which can then be calculated.

Once $K_2$ has been determined, $C_A$ can be calculated for samples of unknown composition. The ratio $I_2^{OI}/I_T$ is obtained from the two detectors, as explained above, d is independently determined using any method known in the art (e.g., beta-absorption), and $C_A$ is calculated directly and rapidly from eqn. 19, without any need for complex computer programs or computers or iterative mathematical procedures.

If detecting the fluorescence from the same face of the sample as the primary beam is incident, eqn. 8 or 14 is used. The unknown constant K is determined using a known sample in the same way as for $K_2$ in eqn. 19, and then for unknowns $C_A$ may be determined directly and rapidly from the ratio $I_2^I/I_T$ using eqn. 8 or 14.

If the concentrations of two or more elements are to be determined, the same apparatus may be used, providing eqn. 12 is met for each element so as to provide full matrix compensation. Eqn. 12 can be met for each element by holding angles $\Phi$ and $\Psi$ constant and changing $E_1$ using filters on a single source or using multiple primary sources, or by varying one or both angles while holding $E_1$ constant, or by a combination thereof.

It will be understood that any standard apparatus may be used in practicing the present invention so long as the equations and assumptions can be satisfied. The samples to be tested and elements to be assayed for can be any for which X-ray fluorescence can be employed. Materials which may be tested include paper, polymeric films, textiles, sheets of rubber, metal foils, and plant leaves, or any other material prepared for testing using methods known in the art (e.g., comminuted and placed in a sample box to provide essentially parallel planar sample faces). The present invention should find particular application in the paper-making field, where it is desired to control carefully the amount of additives in the paper (e.g., compounds containing calcium, barium, or titanium). The thickness of the sample to be tested is limited only by the energy of the fluorescent photons. In the limited sample region being tested, the sample should have essentially parallel planar first and second faces; the rest of the sample may be irregular.

Other variations and modifications will be apparent to those skilled in the art, and the claims are intended to cover all such variations and modifications as fall within the true spirit and scope of the invention.

I claim:

1. An X-ray fluorescence method for determining the mean average concentration of an element in a sample having essentially parallel planar first and second faces in the region being tested, said method comprising:
   (a) aiming a beam of primary photons of a predetermined energy $E_1$ at the first face of the sample such that the beam is at angle $\Phi$ to the first face;
   (b) aiming a first X-ray detector at the second face of the sample to detect the transmitted beam of photons of energy $E_1$;
   (c) aiming a second X-ray detector at the sample at angle $\Psi$ to either face of the sample to detect the beam of characteristic secondary fluorescent photons of energy $E_2$ emitted by the particular element of interest in response to the irradiation by the beam of primary photons wherein $$\frac{\sin \phi}{\sin \psi} \simeq \frac{(E_2)^3}{(E_1)^3} \; ; \text{ and}$$

(d) utilizing the intensities of the transmitted and fluorescent beams to determine said concentration.

2. The method of claim 1 wherein the sample is paper, a polymeric film, a textile, a sheet of rubber, a metal foil, or a plant leaf.

3. The method of claim 1 wherein the sample is paper and the element of interest is calcium, barium, or titanium.

4. The method of claim 1 wherein $\Psi$ is 90 degrees.

5. The method of claim 1 wherein the second detector is aimed at the point of intersection of the line of the beam of primary photons with an imaginary plane parallel to and half-way between the first and second faces of the sample.

6. The method of claim 5 wherein Ψ is 90 degrees.

7. The method of claim 6 wherein the sample is paper, a polymeric film, a textile, a sheet of rubber, a metal foil, or a plant leaf.

8. The method of claim 6 wherein the sample is paper and the element of interest is calcium, barium, or titanium.

* * * * *